(12) United States Patent
Wloch et al.

(10) Patent No.: US 12,162,822 B2
(45) Date of Patent: Dec. 10, 2024

(54) METHOD FOR PRODUCING MENTHOL PARTICLES STABILIZED AGAINST CAKING, AND STORAGE-STABLE MENTHOL PARTICLES AND USE THEREOF

(71) Applicant: BASF SE, Ludwigshafen am Rhein (DE)

(72) Inventors: Sebastian Wloch, Ludwigshafen am Rhein (DE); Gunnar Heydrich, Ludwigshafen am Rhein (DE); Gerd Tebben, Ludwigshafen am Rhein (DE); Matthias Rauls, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 874 days.

(21) Appl. No.: 17/268,591

(22) PCT Filed: Aug. 14, 2019

(86) PCT No.: PCT/EP2019/071770
§ 371 (c)(1),
(2) Date: Feb. 15, 2021

(87) PCT Pub. No.: WO2020/035515
PCT Pub. Date: Feb. 20, 2020

(65) Prior Publication Data
US 2021/0198169 A1     Jul. 1, 2021

(30) Foreign Application Priority Data
Aug. 16, 2018   (EP) .................................. 18189338

(51) Int. Cl.
| | | |
|---|---|---|
| *C07C 29/76* | (2006.01) | |
| *B01D 9/00* | (2006.01) | |
| *B65D 53/00* | (2006.01) | |
| *B65D 81/18* | (2006.01) | |
| *C07C 35/12* | (2006.01) | |

(52) U.S. Cl.
CPC ............ *C07C 29/76* (2013.01); *B01D 9/0004* (2013.01); *B65D 53/00* (2013.01); *B65D 81/18* (2013.01); *C07C 35/12* (2013.01)

(58) Field of Classification Search
CPC ..................................................... C07C 35/12
See application file for complete search history.

(56) References Cited

U.S. PATENT DOCUMENTS

| | | | |
|---|---|---|---|
| 3,023,253 A | 2/1962 | Bain et al. | |
| 3,064,311 A | 11/1962 | Bain et al. | |
| 5,344,860 A | 9/1994 | Pastor et al. | |
| 8,288,593 B2 * | 10/2012 | Rauls ........................ | B01J 2/24 |
| | | | 568/829 |
| 10,589,241 B2 * | 3/2020 | Lenz .......................... | B01J 2/26 |

| | | | |
|---|---|---|---|
| 2005/0169987 A1 | 8/2005 | Korber | |
| 2008/0194883 A1 | 8/2008 | Nowak et al. | |
| 2008/0279947 A1 | 11/2008 | Nowak et al. | |
| 2009/0011238 A1 | 1/2009 | Rheinlander et al. | |
| 2010/0185024 A1 | 7/2010 | Rauls et al. | |
| 2017/0368521 A1 | 12/2017 | Lenz et al. | |

FOREIGN PATENT DOCUMENTS

| | | |
|---|---|---|
| DE | 2530481 A1 | 1/1977 |
| DE | 69307735 T2 | 10/1997 |
| EP | 0210415 A2 | 2/1987 |
| EP | 3059009 A1 | 8/2016 |
| JP | 08-020549 A | 1/1996 |
| JP | 2005-528436 A | 9/2005 |
| JP | 2008-533260 A | 8/2008 |
| JP | 2008-534655 A | 8/2008 |
| JP | 2009-519992 A | 5/2009 |
| JP | 2010-529160 A | 8/2010 |
| JP | 2018-509347 A | 4/2018 |
| WO | 2003/101924 A1 | 12/2003 |
| WO | 2006/097427 A1 | 9/2006 |
| WO | 2006/106130 A1 | 10/2006 |
| WO | 2007/071512 A1 | 6/2007 |
| WO | 2008/152009 A1 | 12/2008 |
| WO | 2016/016154 A1 | 2/2016 |
| WO | 2016/034481 A1 | 3/2016 |

OTHER PUBLICATIONS

"Verfahren zur Herstellung von gegen Verbackung stabilisierten Mentholpartikel sowie lagerstabile Mentholpartikel und ihre Verwendung" IP.COM Journal, IP.COM Inc., West Henrietta, NY, US, Sep. 6, 2018 (Sep. 6, 2018).
Arkenbout, "Melt Crystallization Technology", Technomic Publishing Co. 1995, p. 230.
C. M. Van't Land, "Crystallization of Melts that tend to Supercool", 2005, pp. 161-167.
C.M. Van't Land, "Industrial Crystallization of Melts", Marcel Dekker 2005, pp. 161-167.
European Search Report for EP Patent Application No. 18191869.9, Issued on Feb. 11, 2019, 3 pages.
Fred E. Wright, "The Crystallization of Menthol", Journal of the American Chemical Society, vol. 39, Issue 8, Aug. 1, 1917, pp. 1515-1524.

(Continued)

*Primary Examiner* — Medhanit W Bahta
(74) *Attorney, Agent, or Firm* — Faegre Drinker Biddle & Reath LLP

(57) ABSTRACT

The present invention relates to a process for producing menthol particles stabilized against caking, wherein menthol particles are, following shaping, stored for at least 7 days at a temperature of 0 to 30° C., after which the menthol particles are supplied with a minimum input of mechanical energy. The present invention further relates to storage-stable menthol particles and to the use of said menthol particles in household and consumer goods of all kinds.

13 Claims, No Drawings

(56) References Cited

OTHER PUBLICATIONS

International Preliminary Report on Patentability received for PCT Patent Application No. PCT/EP2019/071770, mailed on Feb. 25, 2021, 15 pages. (8 pages of English Translation and 7 pages of Original Document).
International Search Report and Written Opinion received for PCT Patent Application No. PCT/EP2019/071770, mailed on Nov. 7, 2019, 18 pages. (8 pages of English Translation and 10 pages of Original Document).
Ishchenko, et al., "On the structure of Liquid Systems with the Eutectic State Diagram. 1. Density of Liquid Binary Systems with a Eutectic State Diagram", Ukr. Fiz. Zh., vol. 8, Issue 11, 1963, pp. 1241-1248.
Joel Bernstein, "Polymorphism in Molecular Crystals", Oxford University Press 2002, pp. 94-150.
Kuhnert-Brandstätter et al., "[Thermal analytical investigations on menthols (author's transl)]", Arch. Pharmazie., vol. 307, No. 7, 1974, pp. 497-503.
Tine Arkenbout-De Vroome, "Process Options", Melt Crystallization Technology, 1st Edition, May 2, 1995, p. 230.
Wright et al., "The Crystallization of Menthol.", J. Am. Chem. Soc., vol. 39, No. 8, 1917, pp. 1515-1525.

\* cited by examiner

US 12,162,822 B2

METHOD FOR PRODUCING MENTHOL PARTICLES STABILIZED AGAINST CAKING, AND STORAGE-STABLE MENTHOL PARTICLES AND USE THEREOF

CROSS-REFERENCE TO RELATED APPLICATIONS

This application is a national stage application (under 35 U.S.C. § 371) of PCT/EP2019/071770, filed Aug. 14, 2019, which claims benefit of European Application No. 18189338.9, filed Aug. 16, 2018, both of which are incorporated herein by reference in their entirety.

FIELD OF THE INVENTION

The present invention relates to a process for producing menthol particles stabilized against caking, wherein menthol particles are, following shaping, stored for at least 7 days at a temperature of 0 to 30° C., after which the menthol particles are supplied with a minimum input of mechanical energy. The present invention further relates to storage-stable menthol particles and to the use of said menthol particles in household and consumer goods of all kinds.

STATE OF THE ART

Menthol is a naturally occurring active substance that is used widely in pharmacy, cosmetics, and the food industry. Menthol has a cooling effect on contact with mucous membranes, especially the oral mucosa. In natural sources, for example peppermint oil, menthol occurs in the form of four diastereomeric enantiomer pairs, of which only the main component, (−)-menthol or L-menthol, has the desired gustatory and other sensory properties.

It has long been known that L-menthol can solidify in four different crystal modifications that, while having the same chemical composition, have different physical properties, as previously described in J. Am. Chem. Soc., vol. 39 (8), 1917, pp. 1515 to 1525. For example, the melting points of these various modifications are in particular between 33° C. and 43° C. as described in Archiv der Pharmazie, 307 (7), 1974, pp. 497 to 503. The melting point of the stable alpha-modification is accordingly 42 to 43° C.

Having a melting point of this order means that L-menthol can be supplied to the intermediate or end user either as a melt that is kept liquid in heated containers or in the form of crystals or other solidified shaped bodies. All solids that, like L menthol, have a melting point only just above ambient temperature generally have a high tendency to caking and agglomeration. However, the processing of such caked material is associated with considerable unwanted additional outlay. If pure L-menthol, i.e. menthol not treated with auxiliaries such as separating agents, is to be sold in solid form, the nature of the shaping must ensure that the product reaches the intermediate or end user in free-flowing form.

Menthol is commercially available for example in the form of large crystal needles 0.5 to 3 cm in length and with a thickness from 1 to 3 mm. They are traditionally grown in small amounts from naturally obtained peppermint oil by crystallizing the oil in troughs or vats for some days in cold stores. These crystal needles have good pourability only in the case of short fill heights, but with increased loading and/or at elevated temperature show appreciable caking. Moreover, the nature of their manufacture means that these crystal needles always contain residues of the oil from which they were obtained. The technical outlay involved in crystallizing, separating, and cleaning the crystal needles and the low space-time yield makes such a laborious process unattractive.

DE 25 30 481 relates to a device for crystallizing substances, in particular optically active menthols, that form coarse needle-shaped and bar-shaped crystals under the conditions of crystallization. The crystallization process, which is carried out batchwise, uses a special stirrer that prevents the crystals in the crystal suspension from caking. The desired product is finally isolated using a centrifuge and dried in a drier.

U.S. Pat. Nos. 3,023,253 and 3,064,311 (Bain) describe flaked L-menthol and a method for producing such flakes by applying an L-menthol melt to an cooled immersion roller. If desired, the menthol melt can be introduced between a pair of counterrotating cooled rollers. The menthol film crystallized on the immersion roller is subjected to post-treatment consisting of heat-treatment through an input of heat and reinforcement through the application of additional menthol. The two post-treatments are accomplished simultaneously through the use of an application roller. The flakes thus obtained initially have good pourability. On prolonged storage, caking does however occur.

The principle of further coarsening of the primary particles by compaction is also described in WO 03/101924 (Symrise), which relates to compacted menthol in the form of menthol compacts and also to a process for the production thereof. However, what is noteworthy here is not just the effect of particle size, but the fact that the primary particles need to be present in a specific crystal modification. The compression of crystals that have been obtained from solution crystallization or from flaking with cooled rollers allows compactates to be obtained.

WO 2008/152009 (BASF) describes a process for producing L-menthol in solid form, especially in the form of flakes, by contacting an L-menthol melt with two spaced-apart cooled surfaces, and also the L-menthol in solid form obtainable by said process and the use thereof for incorporation into household and consumer goods of all kinds.

WO 2016/016154 (Symrise) describes a process for producing solid coolants in which a prescratched melt of menthol compounds, i.e. a melt provided with seed crystals, is dripped uniformly onto a precooled surface. The menthol particles in pellet form thus obtained have a convex side and a flat side and a diameter of about 1 to about 20 mm.

EP 3 059 009 A1 (Symrise) describes a process for the caking-free storage of solid coolants in which these are packed in standard packaging having a maximum capacity of 25 l, with the provisos that the packaging is filled to not more than 50% by volume and that the filled contents do not exceed kg in weight.

WO2006/097427 (Symrise) describes menthol-containing solid compositions comprising or consisting of a solid menthol component and a solid silicon dioxide component.

WO2007/071512 (Symrise) describes spherical menthol particles and a process for producing spherical menthol particles in which a menthol melt is dripped into water.

WO 2016/034481 (Sandvik) describes a process and a device for producing L-menthol pellets in which molten droplets of a menthol melt are deposited on a cooling belt via a droplet former and solidified there.

In view of the mentioned prior art, the object of the present invention was to provide storage-stable menthol particles and also a process for producing menthol particles stabilized against caking. It should be possible to operate the process, in particular on an industrial scale, with the minimum possible outlay on equipment and with high throughput; the menthol particles stabilized against caking that are obtained should be free-flowing and, in particular, show only a minimal tendency to caking over a relatively long period of time. In addition, it should be possible to operate the process particularly economically, i.e. cost-effectively. This process should moreover be suitable for menthol particles of a very wide variety of shapes.

DESCRIPTION OF THE INVENTION

The present invention provides a process for producing menthol particles stabilized against caking, wherein menthol particles are, following shaping, stored for at least 7 days at a temperature of 0 to 30° C., after which the menthol particles are supplied with at least as much mechanical energy as they receive when
  20 kg of said menthol particles
    are packed into a bag made from polyethylene film 0.12 mm thick having the dimensions length L (bag) 660 mm and width W (bag) 690 mm, sealing the bag;
    this bag is packed into a cuboidal box made from double-walled corrugated cardboard having the internal dimensions length L (box) 385 mm, width W (box) 320 mm, and height H (box) 450 mm and a corrugated cardboard thickness of 6 mm, and
    this box is dropped once from a height of 1.0 m onto an inelastic surface plane-parallel to the side formed by L (box) and H (box).

The phenomenon known as caking or agglomeration is probably essentially attributable to particles combining to form agglomerates. It has surprisingly been found that menthol particles obtainable with the process of the invention are stabilized against caking. This means in particular that the number of particles in a collective decreases less sharply when stored for more than 18 weeks at 20° C. than does the number of particles in a comparison collective that was not subjected to the process of the invention. The menthol particles thus obtainable are free-flowing even after storage for more than 18 weeks at 20° C. and can thus be used for example directly, without additional expenditure of energy, for the production of household and consumer goods such as cosmetic and pharmaceutical products or foodstuffs and confectionery.

The process of the invention is characterized by two steps. In a first step, the menthol particles to be used as starting products for the process of the invention are, following shaping, stored for at least 7 days at a temperature of 0 to 30° C. This is followed by a second step in which mechanical energy is supplied to the stored menthol particles. In this step, the menthol particles are supplied with at least as much mechanical energy as they receive when
  20 kg of said menthol particles
    are packed into a bag made from polyethylene film 0.12 mm thick having the dimensions length L (bag) 660 mm and width W (bag) 690 mm, sealing the bag;
    this bag is packed into a cuboidal box made from double-walled corrugated cardboard having the internal dimensions length L (box) 385 mm, width W (box) 320 mm, and height H (box) 450 mm and a corrugated cardboard thickness of 6 mm, and this box is dropped once from a height of 1.0 m onto an inelastic surface plane-parallel to the side formed by L (box) and H (box).

The storage following shaping can take place at temperatures from 0 to 30° C., preferably at temperatures from 5 to 25° C., in particular from 10 to 23° C., preferably from 12 to 20° C. The storage is for at least 7 days. The storage can be carried out for example for 10 days at 20° C. or for 21 days at 18° C.

The storage time begins at the end of shaping of the menthol particles to be used. This is the point at which the menthol particles to be used have obtained their desired shape, size, and/or size distribution.

The storage period is not critical, provided that the 7 days have been reached. Storage times of for example 14 days, 21 days or even several months, for example 1, 2, 6 or 12 months or one or more years, are therefore conceivable. The storage is usually for at least 7 days up to 3 months, in particular up to 4 months, in particular up to 6 months.

The storage conditions other than the temperature and minimum storage period are not critical. The storage can be carried out in customary packaging units such as bags, sacks, boxes, drums or combinations thereof. When packing the menthol particles into the packaging units, it is advantageous to ensure that the temperature does not fall below the dew point, in order that no condensation forms in the packaging unit. It is advantageous if the temperature does not fall below the dew point during storage either. The storage is preferably carried out at a relative humidity of less than 65%.

Ideally, both the storage and the input of mechanical energy are carried out in one and the same packaging unit, for example in a box as described below, a drum, sack, bag or similar customary containers.

In one embodiment of the invention, both steps of the process of the invention are carried out in one packaging unit.

The input of mechanical energy can be supplied in a variety of ways. What is critical is that the menthol particles are supplied with at least as much energy as they receive when
  20 kg of said menthol particles
    are packed into a bag made from polyethylene film 0.12 mm thick having the dimensions length L (bag) 660 mm and width W (bag) 690 mm, sealing the bag;
    this bag is packed into a cuboidal box made from double-walled corrugated cardboard having the internal dimensions length L (box) 385 mm, width W (box) 320 mm, and height H (box) 450 mm and a corrugated cardboard thickness of 6 mm, and
    this box is dropped once from a height of 1.0 m onto an inelastic surface plane-parallel to the side formed by L (box) and H (box).

The amount of mechanical energy to be supplied can be provided as a single input of energy or as the repeated input of smaller subquantities of energy.

Examples of suitable forms for the input of mechanical energy are horizontal impact against a wall; an input of energy via a weight or punch onto the stationary menthol particles, preferably an input in the form of a sudden impact; active accelerated vertical fall or free fall. In a preferred embodiment of the present process, the input of mechanical energy is supplied by free fall onto an inelastic surface. The fall height can for example be within a range from 1.0 to 5 m, for example within a range from 1 to 3 m, for example 1.5 m or 2 m.

In one embodiment of the present invention, the mechanical energy can be supplied when 20 kg of menthol particles
  are packed into a bag made from polyethylene film 0.12 mm thick having the dimensions length L (bag) 660 mm and width W (bag) 690 mm, sealing the bag;
  the bag is packed into a cuboidal box made from double-walled corrugated cardboard having the internal dimensions length L (box) 385 mm, width W (box) 320 mm, and height H (box) 450 mm and a corrugated cardboard thickness of 6 mm, and this box is dropped once from a height of at least 1.0 m up to a height of 5 m, preferably a height of up to 3 m, onto an inelastic surface plane-parallel to the side formed by L (box) and H (box).

It has surprisingly been found that, through the combination of storage in accordance with the invention and an input of mechanical energy in accordance with the invention, it possible to obtain advantageous menthol particles stabilized against caking.

With the process of the invention it is possible to obtain menthol particles stabilized against caking and in which the shape, size or number of the particles largely correspond to those of the menthol particles used.

In one embodiment of the process, said process is executed such that the number of particles at the end of the process is still at least 50%, in particular at least 60%, preferably at least 70%, preferably at least 80%, of the number of particles employed at the start of the process.

In one embodiment of the process, said process is executed such that at least 50% by weight, in particular at least 60% by weight, preferably at least 70% by weight, preferably at least 80% by weight, of the menthol particles stabilized against caking of the invention are of the same shape as the menthol particles employed.

In one embodiment of the process, said process is executed such that at least 50% by weight, in particular at least 60% by weight, preferably at least 70% by weight, preferably at least 80% by weight, of the menthol particles stabilized against caking of the invention are of the same size as the menthol particles employed.

Those skilled in the art can execute these embodiments, for example by limiting the input of mechanical energy or through the nature of the selected input of mechanical energy.

In one embodiment of the process, said process is executed such that the menthol particles are supplied with only enough energy that at least 50% by weight, preferably at least 60% by weight, in particular at least 70% by weight, preferably at least 80% by weight, of the particles retain their size.

In one embodiment of the process, said process is executed such that the menthol particles are supplied with only enough energy that at least 50% by weight, preferably at least 60% by weight, in particular at least 70% by weight, preferably at least 80% by weight, of the particles retain their shape.

Menthol particles are for the purposes of the invention understood as meaning discrete particles of menthol in solid form.

The terms "menthol particles", "menthol particles to be used" and "menthol particles used" refer to the particles to be used as starting products for the process of the invention. The term "menthol particles stabilized against caking" refers to the particles obtainable by the process of the invention.

The size of the menthol particles refers to the longest dimension in space of a particle of any shape. Thus, in the case of menthol particles that are spherical in shape, the size of the particle is the diameter of the sphere; in the case of menthol particles that are cuboidal in shape, the size of the particle is the diagonal of the cuboid.

In a preferred embodiment of the invention, menthol particles are used that have a size within a range from 1 to 35 mm, in particular from 4 to 35 mm, in particular from 5 to 30 mm, preferably from 10 to 25 mm, preferably from 12 to 24 mm, in particular 15 to 20 mm.

In a preferred embodiment of the invention, menthol particles are used that have a size within a range from 4 to 35 mm, in particular within a range from 5 to 30 mm, preferably from 10 to 25 mm, preferably within a range from 12 to 24 mm, in particular 15 to 20 mm and the content thereof of menthol particles under 4 mm in size is less than 5% by weight, preferably less than 2% by weight, and in particular less than 1% by weight, very preferably less than 0.5% by weight, particularly preferably less than 0.1% by weight.

The size of the particles and the particle size distribution can be determined for example microscopically or by sieve analysis.

Shaped bodies refer to the geometry of a three-dimensional figure that is described by its surfaces. The surface of a shaped body may be made up of flat or convex surfaces. The term shape is hereinafter used synonymously with the term shaped body.

Menthol particles are known in a wide variety of shaped bodies, for example crystal needles, polyhedra, cubes, cuboids; cones, prisms, spheres, hemispheres, spherical disks, cylinders, beads, and also mixed forms thereof, etc. The shaped bodies result here from the nature of production:

Crystal needles are obtained for example by crystallizing L-menthol from an L-menthol-containing solution or melt. Crystal needles typically have a length from 0.5 to 3 cm and a thickness from 1 to 3 mm. Crystal needles are, as a consequence of their manufacturing process, characterized by the shaped body having a geometry in which only one dimension in space is a multiple of the other dimensions in space. Compacts (synonym: compacted crystals/tablets) are obtained by compression of crystals and, depending on the compression mold, can be in the form of e.g. spheres, cubes, cuboids, pincushions or strands. Pellets can be obtained for example by dripping menthol melts onto a cooled surface. Spherical particles can be obtained for example by dripping menthol melts into water. Flakes can be obtained for example by contacting a menthol melt with two spaced-apart cooled surfaces.

The process of the invention is suitable for menthol particles of any shape. Preferred menthol particles are for the purposes of the invention menthol particles in the form of flakes, spheres or pellets. Particular preference is given to menthol particles in the form of flakes.

Flakes are for the purposes of the present invention shaped bodies in which at least two surfaces of the shaped bodies are parallel to one another. Flakes are for the purposes of the present invention understood as meaning in particular shaped bodies in which the two largest surfaces of the shaped bodies are parallel to one another.

The distance between the two parallel surfaces is referred to as the thickness of the flake. If more than two surfaces are parallel to one other, the smallest distance between two such surfaces is referred to as the thickness of the flake.

Flakes are to be understood as meaning in particular shaped bodies in which at least two surfaces are parallel to one another and in which the other dimensions of the shaped body in space (referred to as the mean edge length of the flake) are at least 1.25 times the thickness. Flakes are to be understood as meaning in particular shaped bodies in which at least two surfaces are parallel to one another, with the exception of shaped bodies in which only one dimension of the shaped body in space is a multiple (at least three times) of the thickness.

Examples of flakes thus include cuboids or cubes. Flakes are in addition shaped bodies produced by comminution, in particular breakage, of a film and in which the surfaces not formed by the parallel surfaces are not formed at right angles to the surfaces formed by the parallel surfaces.

Spheres are for the purposes of the present invention shaped bodies in which all surfaces of the shaped body are convex. Examples of spheres thus include balls, pincushions or beads.

Pellets are for the purposes of the present invention shapes characterized by having a planar surface and a convex surface on the opposite side to the planar surface.

Examples of menthol particles suitable as starting products for the process of the invention are the flakes described in WO2008/152009 (BASF) or U.S. Pat. Nos. 3,023,253 and 3,064,311, pellets described in WO 2016/034481 (Sandvik), pellets described in WO2016/016154 (Symrise) or compacts described in WO 03/101924 (Symrise).

Particular preference is given to menthol particles in which the menthol is present in the form of L-menthol. Particular preference is given to menthol particles in which the menthol content, in particular the L-menthol content, is more than 80% by weight, in particular more than 90%, in particular more than 99.5%, preferably more than 99.7% by weight, based on the total weight of the particle.

Melts of L-menthol of the formula (I) are suitable as starting material for producing the menthol particles to be used in accordance with the invention,

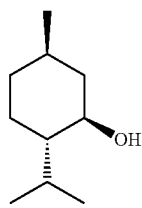

(I)

IUPAC name: 1R,2S,5R-2-isopropyl-5-methylcyclohexanol wherein the molten menthol may be of natural or synthetic origin and has an enantiomeric excess of usually at least 95%, 96% or 97% ee to 100% ee, preferably 98%, 98.5% or 99% to 99.9% ee. Particularly suitable starting materials in the context of the process of the invention are melts of L-menthol that have a content of L-menthol of at least 95%, 96% or 97% by weight or above, preferably at least 98% to 100% by weight and very particularly preferably 98%, 98.5% or 99% to 99.9% by weight (in each case based on the total weight of the melt), alongside impurities such as residual solvents, diastereomers of L-menthol of the formula (I) or by-products from methods of synthesis or isolation.

Preference is given to using an L-menthol melt that comprises 0.1% to 50% by weight, in particular 1% to 40% by weight, in particular 5% to 35% by weight, preferably 10% to 30% by weight, of seed crystals of menthol.

The percentage by weight of seed crystals is in each case based on the total weight of the mixture of melt and seed crystals to be used.

Preference is given to using an L-menthol melt that comprises 0.1% to 50% by weight, in particular 1% to 40% by weight, in particular 5% to 35% by weight, preferably 10% to 30% by weight, of seed crystals of menthol, the remaining parts by weight being made up of the amount of L-menthol in molten form.

An L-menthol melt is therefore to be understood as meaning for example L-menthol that comprises 50% to 99.9% by weight, 60% to 99% by weight, in particular 65% to 95% by weight, preferably 70% to 90% by weight, of menthol in molten form.

The L-menthol melt that is preferably to be used is accordingly a suspension of seed crystals and molten L-menthol.

The crystals of L-menthol referred to as seed crystals can for example be obtained in a customary manner by crystallizing L-menthol from an L-menthol-containing solution or melt and added to the L-menthol melt. This can be done for example by stirring into a reservoir vessel or sprinkling precrushed crystals of L-menthol onto the L-menthol melt (liquid crystal film) used. It is also possible to produce the seed crystals using a scraped-surface cooler or extruder as described hereinbelow and to add these to the L-menthol melt. It is further possible to use as seed crystals the fines fraction described below.

It is also possible to produce the seed crystals in the L-menthol melt before contacting with the cooled surface. Examples of suitable methods for producing the seed crystals in the L-menthol melt are the use of a scraped-surface cooler or the use of an extruder.

One embodiment of the invention is characterized by the seed crystals being formed by treatment in a scraped-surface cooler of the menthol melt to be used.

In a preferred embodiment, seeding is achieved by passing the melt through a heat exchanger operated below the melting point, the walls of which are freed of crystallized material by an abrasive element, the abrasive element consisting of at least one planar element, preferably a plurality thereof. Examples of planar elements are scrapers. Such arrangements are known as scraped-surface coolers and are described for example in G. Arkenbout, Melt Crystallization Technology, Technomic Publishing Co. 1995, p. 230. Suitable scraped-surface coolers have for example a circular-cylindrical, cooled inner surface that is swept by scrapers arranged on a rotating shaft.

In one embodiment, seed crystals of L-menthol are used that are obtained by treatment in a scraped-surface cooler of the L-menthol melt to be used, the seed crystals being formed in situ in the L-menthol melt to be solidified, thereby avoiding an additional work step.

In one embodiment, the temperature in the scraped-surface cooler is set to a range from 10 to 32° C., in particular from 15 to 20° C. The temperature can be set by means of a liquid coolant, in particular water. The menthol melt can be conveyed through the scraped-surface cooler in a single pass. It is likewise possible to circulate the menthol melt through the scraped-surface cooler multiple times until the desired proportion of seed crystals has been produced.

One embodiment is characterized by the seed crystals being formed by treatment in an extruder of the menthol melt to be used.

A heat exchanger having an abrasive element that comprises at least one helical element is for the purposes of the invention referred to as an extruder. Such arrangements are described for example in C. M. Van't Land, Industrial Crystallization of Melts, Marcel Dekker 2005, pp. 161-167.

The abrasive element can comprise one or more devices having helical elements, for example one screw or in particular two screws (so-called twin screw). The devices may be in a corotating or counterrotating arrangement. The devices may be in an interlocking or a non-interlocking arrangement. In addition to the helical elements, which generally serve primarily for conveyance, each device of the abrasive element can comprise further elements that usually serve primarily for mixing. Examples of such elements are kneading blocks. The device of the abrasive element usually has different zones of helical elements and mixing elements.

In one embodiment, a heat exchanger having a counter-rotating twin screw is used as the extruder.

In one embodiment, a heat exchanger having a corotating twin screw is used as the extruder. Preference is given to using as the extruder a heat exchanger having a corotating twin screw in which the screws are in an interlocking arrangement.

In one embodiment, the temperature of the extruder is set to below 42° C., preferably to a temperature from 5 to 40° C., in particular to a range from 10 to 32° C., in particular from 15 to 20° C. In a further embodiment, the temperature of the extruder at the inlet and/or at the outlet can be set to higher temperatures than in the region inbetween. The temperature can be set by means of a liquid coolant, in particular water. The menthol melt can be conveyed through the extruder in a single pass. It is likewise possible to circulate the menthol melt through the extruder multiple times until the desired proportion of seed crystals has been produced.

In one embodiment, seed crystals of L-menthol are used that are obtained by treatment in an extruder of the L-menthol melt to be used in accordance with the invention, the seed crystals being formed in situ in the L-menthol melt to be solidified, thereby avoiding an additional work step.

The proportion of seed crystals in the menthol melt can be determined for example by measuring the density, measuring the viscosity of the L-menthol melt, the power consumption of the scraped-surface cooler or optically, for example with the aid of a scattered-light probe.

In a preferred embodiment, the proportion of seed crystals in the L-menthol melt is determined by measuring the density. The density of L-menthol crystals in the alpha modification is 900 kg/m$^3$ at 15° C. The density of menthol melts at various temperatures is described for example in Ishchenki, E. D.; Roshchina, G. P. Ukr Fiz Zh Ukr. Ed., 1963, vol. 8, issue 11 pages 1241-1249.

The proportion of seed crystals is usually measured at the outlet of the scraped-surface cooler or extruder. If the desired proportion of seed crystals is not achieved, the menthol melt can be fed back into the scraped-surface cooler or extruder for however long it takes for the desired proportion of seed crystals in the menthol melt to be achieved. Alternatively, seed crystals can be added to the L-menthol melt.

The L-menthol melt to be used for the producing the menthol particles is usually used at a temperature within a range of about 40 to 60° C., preferably about 43 to 50° C. In the temperature range from below 42 to 43° C., i.e. below the melting point of L-menthol, L-menthol melts are super-cooled melts.

In a preferred embodiment of the process of the invention, menthol particles in the form of flakes are used. These can be obtained for example by applying a melt of L-menthol to a cooled surface such as an immersion roller. The menthol film crystallized on the immersion roller can be subjected to post-treatment consisting of heat-treatment through an input of heat and reinforcement through the application of additional menthol. Menthol particles in the form of flakes can also be obtained for example by applying a menthol melt between a pair of counterrotating, cooled rollers.

In a preferred embodiment of the process, menthol particles in the form of flakes are used that have a thickness from 0.2 to 15 mm, preferably from 4 to 10 mm, in particular 6 to 8 mm.

In a preferred embodiment of the process, menthol particles in the form of flakes are used that have an average edge length from 5 to 25 mm, preferably 12 to 16 mm.

In a preferred embodiment of the process, menthol particles in the form of flakes are used that have a thickness from 0.2 to 15 mm, preferably from 4 to 10 mm, in particular 6 to 8 mm, and an average edge length from 5 to 25 mm, preferably 12 to 16 mm.

In a preferred embodiment of the process, menthol particles in the form of flakes are used that have a size within a range from 1 to 35 mm, in particular from 4 to 35 mm, in particular from 5 to 30 mm, preferably from 10 to 25 mm, preferably from 12 to 24 mm, in particular 15 to 20 mm.

In a preferred embodiment of the process, menthol particles in the form of flakes are used that have a size within a range from 4 to 35 mm, in particular within a range from 5 to 30 mm, preferably from 10 to 25 mm, preferably within a range from 12 to 24 mm, in particular 15 to 20 mm and the content thereof of menthol particles under 4 mm in size is less than 5% by weight, preferably less than 2% by weight, and in particular less than 1% by weight, very preferably less than 0.5% by weight, particularly preferably less than 0.1% by weight.

In a preferred embodiment of the process, menthol particles in the form of flakes are used that are obtained by contacting a menthol melt with two spaced-apart cooled surfaces, this being accompanied by solidification of the menthol melt into menthol, with the contact between the solidifying menthol melt and the cooled surfaces maintained at least until solidification is complete.

It is advantageous to use the menthol melts described above. Preference is given to using an L-menthol melt that comprises 0.1% to 50% by weight, in particular 1% to 40% by weight, in particular 5% to 35% by weight, preferably 10% to 30% by weight, of seed crystals of menthol.

The L-menthol melt can be transported to the two spaced-apart cooled surfaces for example via a weir or via a thermostatically controlled pipeline.

In this embodiment, the L-menthol melt used is brought into contact with two spaced-apart cooled surfaces. The L-menthol melt used is preferably present in the intermediate space between the two spaced-apart cooled surfaces. The contacting of the melt with the individual surfaces can take place simultaneously, i.e. at the same time, or at a staggered interval.

Processing requirements normally mean that contacting of the L-menthol melt used with the two cooled surfaces takes place at a staggered interval, for example by first applying the melt to an area of one of the two surfaces that is not actively cooled; this is then cooled for a short time and additionally comes into contact with the second cooled surface.

Processing requirements normally mean that contacting of the employed L-menthol melt with the two cooled surfaces takes place at a staggered interval such that the melt comes into contact with one of the cooled surfaces first and additionally with the second cooled surface shortly thereafter. It has proven advantageous here to keep the time interval between contacting of the L-menthol melt with each of the cooled surfaces as short as possible so that, depending on the temperature difference between the L-menthol melt used and the cooled surface contacted first, no extensive or complete solidification of the L-menthol melt used has taken place before contact with the second cooled surface is established. The time interval between contacting of the employed L-menthol melt with the respective surfaces is usually not more than 30 s, preferably up to 20 s, and more preferably up to 10 s.

In one embodiment, the cooled surfaces to be used are in each case smooth surfaces, preferably flat sections of continuous belts made from steel, other metals, plastics or combinations of said materials. Particular preference is given to continuous belts made from smooth or polished stainless steel.

The duration of contact with the two cooled surfaces of the melt used, or of the solidifying melt, referred to hereinbelow as the contact time, can be of identical or different length for individual surfaces. The contact time of the melt with the respective cooled surfaces is usually of different duration, since, as described above, contacting often takes place at a staggered interval, the end of the contact time normally being staggered too, i.e. the ending of contact of the completely solidified L-menthol melt with the respective cooled surface takes place at different times. Whatever the order in which contacting of the melt with each of the two cooled surfaces and detachment of the completely solidified L-menthol melt from the surfaces take place, the contact times for the individual cooled surfaces overlap such that the employed L-menthol melt/the solidifying L-menthol melt is in contact with both cooled surfaces simultaneously for a selectable period of time.

In this embodiment, the contact between the solidifying L-menthol melt and the cooled surfaces is maintained at least until solidification is complete. The solidification/crystallization of the L-menthol melt used is preferably not considered complete until at least about 80% by weight or better 85% to 100% by weight, preferably 90% to 100% by weight, preferably 95% or 97% to 99.5% by weight, and very particularly preferably 98% to 99% by weight, of the resulting L-menthol in solid form is present in the alpha modification. The particular modification of the solidified L-menthol obtained can be determined using methods known to those skilled in the art, such as X-ray diffraction or powder diffractometry (see e.g. Joel Bernstein, Polymorphism in Molecular Crystals, Oxford University Press 2002, pp. 94-150).

The term "cooled surfaces" is to be understood as meaning surfaces that have a temperature below the melting/solidification point of L-menthol of 42 to 43° C. or are thermostatically controlled at such a temperature. The cooled surfaces to be used each have, independently of one another, a temperature usually within a range from about 0 to about 40° C., preferably from about 0 to about 35° C., particularly preferably from 5 to 30° C., and very particularly preferably within a range from 10 to 25° C., in particular from 15 to 20° C. The two surfaces can here both have the same temperature or a different temperature. It is also possible to change the temperature of the cooled surfaces individually in the course of the respective contact time, i.e. to increase or decrease it.

In a preferred embodiment, the two cooled surfaces have a plane-parallel orientation and are spaced apart at a distance of usually 0.2 to 15 mm, preferably 2 to 10 mm, in particular 3 to 9 mm, in particular 5 to 8 mm, in particular 6 to 8 mm.

The term plane-parallel orientation is to be understood as meaning that the two cooled surfaces are, within the limits of usual measuring accuracy, the same distance apart over the entire area or part-area that is contacted with the L-menthol melt to be solidified. It is advantageous if the intermediate space formed between the two cooled surfaces is completely filled with L-menthol, since this ensures the largest possible contact area between the cooled surfaces and the L-menthol melt to be solidified.

Depending on the proportion of seed crystals in the L-menthol melt used, the selected temperatures of the L-menthol melt used, and the distance apart and temperatures of the two cooled surfaces, the contact time of the solidifying L-menthol melt with the two cooled surfaces is chosen such that solidification is complete. Usual contact times are within a range from 10 to 300 s, preferably 120 to 240 s. Solidification is usually complete after a contact time of about 10 to about 300 s, preferably about 20 to about 250 s, preferably up to about 200 s and very particularly preferably from 30 to 150 s, preferably up to 100 s. The specified contact times are to be understood here as stating the time intervals during which there is simultaneous contact between the L-menthol melt/the solidifying or already solidified L-menthol melt at both cooled surfaces. It is also possible for the contact of the solidified L-menthol melt with one of the two cooled surfaces to be extended beyond this time.

In a preferred embodiment, short contact times and complete solidification can be achieved by adding seed crystals to the melt as described above, before or during contacting with the cooled surfaces.

In a particularly preferred embodiment, the process is executed using a double-belt cooler. Double-belt coolers are known to those skilled in the art and can be obtained for example from Ipco Germany GmbH, 70736 Fellbach, Germany or SBS Steel Belt Systems S.r.L., Italy.

If using the double-belt cooler mentioned, the cooled surfaces to be used are realized in the form of two continuous belts (cooling belts), usually made of steel, guided over rollers in opposite direction of rotation (see C. M. van't Land, Industrial Crystallization of Melts, Marcel Dekker 2005, p. 63). The solidification of the L-menthol melt into L-menthol in solid form then takes place in the intermediate space between the plane-parallel sections of the two cooling belts of the double-belt cooler that face one another.

In order that the contacting of the L-menthol melt to be solidified with the two cooling belts is achieved as simultaneously as possible, it is advisable to bring the melt into contact with the cooling belts as close as possible to the point at which the intermediate space between the plane-parallel sections of the two cooling belts begins, so that premature solidification of the L-menthol melt is kept to a minimum.

The preferred process for producing menthol particles in the form of flakes can be carried out batchwise, for example using cooled punches, or continuously, for example using a double-belt cooler as mentioned above. The continuous process in particular has economic advantages here.

The solidified L-menthol film obtained can then be removed from the cooled surface(s) by methods known to those skilled in the art. Depending on how the process is executed, the L-menthol film falls directly from the cooled surface or it can be detached from one or both of the cooled surfaces by means of a knife attachment. On detaching the solidified L-menthol film from one or both of the cooled surfaces, preferably the cooling belts of a double-belt cooler that is preferably used, L-menthol particles in the form of flakes are obtained.

These can be adjusted to L-menthol flakes of the desired size by means of suitable post-treatment methods. Examples of post-treatment methods include comminution, for example comminution using pin crushers, cam crushers, single-shaft crushers, rotary shears, impact crushers or using jaw crushers, and also comminution through sieving. Comminution is preferably carried out using grinders operated at slow speeds, for example within a range from 0.2 m/s to 10 m/s, in particular within a range from 0.5 m/s to 2.0 m/s.

In addition, particles of a particular size can be removed by sieving. The post-treatment methods mentioned may be employed in any combination with one another.

The menthol particles in flake form thus obtained can be additionally treated (before or after any optional post-treatment carried out) by further cooling, for example on a cooled screw conveyor or a cooled conveyor belt.

Through the preferred method for producing menthol particles in the form of flakes, it is possible to obtain L-menthol particles in the form of flakes that, as a result of solidification in contact with two cooled surfaces, have at least two smooth surfaces.

Depending on the selected distance between the two cooled surfaces, the menthol particles obtainable by the preferred process for producing menthol particles in flake form have a thickness from 0.2 to 15 mm, preferably 2 to 10 mm, in particular 3 to 9 mm, in particular 5 to 8 mm, in particular 6 to 8 mm.

The size of the flakes can be freely chosen in accordance with the nature of post-treatment and ranges from continuous strips to substantially comminuted flakes. In one embodiment, particles under 4 mm in size (the so-called fines fraction) can be removed, for example by sieving. In one embodiment, the fines fraction thus separated can then be added as seed crystal to the L-menthol melt to be solidified.

In a preferred embodiment, menthol particles in the form of flakes are obtained that have a size within a range from 1 to 35 mm, in particular from 4 to 35 mm, in particular from 5 to 30 mm, preferably from 10 to 25 mm, preferably from 12 to 24 mm, in particular 15 to 20 mm.

In a preferred embodiment, menthol particles in the form of flakes are obtained that have a size within a range from 4 to 35 mm, in particular from 5 to 30 mm, preferably from 10 to 25 mm, preferably from 12 to 24 mm, in particular 15 to 20 mm, and the content thereof of menthol particles under 4 mm in size is less than 5% by weight, preferably less than 2% by weight, and in particular less than 1% by weight, very preferably less than 0.5% by weight, particularly preferably less than 0.1% by weight.

The L-menthol particles in flake form thus obtainable are particularly suitable as menthol particles to be used for producing menthol particles stabilized against caking.

The invention further provides for the use of the menthol particles stabilized against caking obtainable by the process of the invention in the production of, or in, household and consumer goods such as pharmaceutical or cosmetic products, foodstuffs, hygiene or cleaning articles, confectionery or tobacco products.

The invention further provides menthol particles stabilized against caking obtainable by the process of the invention.

A general problem with the storage of menthol particles is their limited shelf life. Menthol particles, especially in the form of flakes, spheres and pellets, exhibit so-called caking phenomena after storage. This places considerable limits on the use of the stored particles.

One object of the present invention was therefore to provide menthol particles that have increased storage stability.

It has surprisingly been found that menthol particles obtainable when 20 kg of menthol particles, following shaping, a) are packed into a bag made from polyethylene film 0.12 mm thick having the dimensions length L (bag) 660 mm and width W (bag) 690 mm, sealing the bag; this bag is packed into a cuboidal box made from double-walled corrugated cardboard having the internal dimensions length L (box) 385 mm, width W (box) 320 mm, and height H (box) 450 mm and a corrugated cardboard thickness of 6 mm, b) this box is stored for 10 days at 20° C. on the side formed from L (box) and H (box), and c) this is then dropped once from a height of 1.5 m onto an inelastic surface plane-parallel to the side formed by L (box) and H (box), have increased storage stability.

The present invention further provides storage-stable menthol particles obtainable when 20 kg of menthol particles, following shaping, a) are packed into a bag made from polyethylene film 0.12 mm thick having the dimensions length L (bag) 660 mm and width W (bag) 690 mm, sealing the bag; this bag is packed into a cuboidal box made from double-walled corrugated cardboard having the internal dimensions length L (box) 385 mm, width W (box) 320 mm, and height H (box) 450 mm and a corrugated cardboard thickness of 6 mm, b) this box is stored for 10 days at 20° C. on the side formed from L (box) and H (box), and c) this is then dropped once from a height of 1.5 m onto an inelastic surface plane-parallel to the side formed by L (box) and H (box), where the storage stability $S=[(Z_1-Z_2)/Z_1]$, is less than or equal to 0.25, in particular less than or equal to 0.2, preferably less than or equal to 0.1, where $Z_1$ is the number of particles after shaping and $Z_2$ the number of particles 20 weeks after shaping.

As a measure of the storage stability S, the number of particles is determined immediately after shaping and after 20 weeks.

The storage stability is for the purposes of the present invention defined as $S=[(Z_1-Z_2)/Z_1]$, where $Z_1$ is the number of particles after shaping and $Z_2$ the number of particles 20 weeks after shaping.

For the determination of the number of particles $Z_1$, a defined mass of particles (e.g. 100 g) is weighed out and counted after shaping. For the determination of the number of particles $Z_2$, an equal mass of particles (e.g. 100 g) is weighed out and counted 20 weeks after shaping. The number of particles can be determined for example microscopically.

In the 20 weeks from shaping to determination of the particles, the particles are usually kept at temperatures from 0 to 30° C., in particular from 20 to 25° C., in particular at 20° C.

In a preferred embodiment of the invention, the storage stability S is less than or equal to 0.2; in particular less than or equal to 0.1, in particular less than or equal to 0.05; preferably less than or equal to 0.01; in particular less than or equal to 0.001.

An increase in the number of particles, for example as a result of a stabilization measure carried out, is also encompassed by the present invention.

In a further embodiment of the invention, the storage stability is within a range from −0.25 to 0.25; in particular from −0.2 to 0.2, preferably from −0.1 to 0.1, in particular from −0.05 to 0.05, preferably from −0.001 to 0.001.

The number of particles 20 weeks after shaping is preferably identical to the number of particles after shaping; if this is the case, the storage stability is S=0.

In one embodiment of the invention, the storage stability S is within a range from 0 to 0.25; in particular within a range from 0 to 0.2; in particular from 0 to 0.1; in particular from 0 to 0.05; in particular from 0 to 0.01; in particular from 0 to 0.001.

All of the abovementioned menthol particles are suitable as storage-stable menthol particles.

A preferred embodiment of the invention provides storage-stable menthol particles that have a size within a range from 1 to 35 mm, in particular from 4 to 35 mm, in particular from 5 to 30 mm, preferably from 10 to 25 mm, preferably from 12 to 24 mm, in particular 15 to 20 mm.

A preferred embodiment of the invention provides storage-stable menthol particles that have a size within a range from 4 to 35 mm, in particular within a range from 5 to 30 mm, preferably from 10 to 25 mm, preferably within a range from 12 to 24 mm, in particular 15 to 20 mm, and the content thereof of menthol particles under 4 mm in size is less than 5% by weight, preferably less than 2% by weight, and in particular less than 1% by weight, very preferably less than 0.5% by weight, particularly preferably less than 0.1% by weight.

Particular preference is given to storage-stable menthol particles in which the menthol content, in particular the L-menthol content, is more than 80% by weight, in particular more than 90%, in particular more than 99.5%, preferably more than 99.7% by weight, based on the total weight of the particle.

Particular preference is given to storage-stable menthol particles in which the menthol is present in the form of L-menthol.

Particular preference is given to storage-stable menthol particles present in the form of flakes, spheres or pellets, preferably in the form of flakes.

Further preference is given to storage-stable menthol particles present in the form of flakes having a thickness from 0.2 to 15 mm, preferably from 4 to 10 mm, in particular 6 to 8 mm.

Especial preference is given to storage-stable menthol particles menthol in the form of flakes obtained by contacting an menthol melt with two spaced-apart cooled surfaces, this being accompanied by solidification of the menthol melt into menthol, with the contact between the solidifying menthol melt and the cooled surfaces maintained at least until solidification is complete.

The storage stability of the storage-stable menthol particles thus obtainable makes them suitable in particular for the production of or use in household and consumer goods.

The invention therefore further provides for the use of storage-stable menthol particles obtainable according to the invention in the production of, or in, household and consumer goods such as pharmaceutical or cosmetic products, foodstuffs, hygiene or cleaning articles, confectionery or tobacco products.

A further object of the present invention was to provide a process that makes it possible to obtain menthol melts having a defined content of seed crystals that is as high as possible. Such a process should advantageously permit long operating times.

It has surprisingly been found that an extruder is suitable for producing crystals of menthol. Such crystals thus obtained can for example be used directly or converted by compression into various shaped bodies. The crystals can also be added to a menthol melt, for example as seed crystals, and this menthol melt provided with seed crystals can then be used for example in the production of menthol particles in a wide variety of forms, such as in the form of flakes or in the form of pellets. It has surprisingly also been found that it is possible with the process of the invention to adjust a menthol melt to a desired content of menthol crystals and to use the thus obtained suspension of menthol crystals and molten menthol for the production of menthol particles in a wide variety of forms, such as in the form of flakes or in the form of pellets. Compared to the known prior art process for producing menthol melts having defined contents of seed crystals, the process of the invention has the distinguishing feature of increased operating times.

The invention therefore further provides a process for producing crystals of menthol, in particular L-menthol, wherein a menthol melt is conveyed through an extruder.

The invention therefore further provides a process for producing a menthol melt, in particular an L-menthol melt, that comprises 0.1% to 50% by weight of seed crystals of menthol, in particular L-menthol, wherein a menthol melt is conveyed through an extruder.

A heat exchanger having an abrasive element that comprises at least one helical element is for the purposes of the invention referred to as an extruder. Such arrangements are described for example in C. M. Van't Land, Industrial Crystallization of Melts, Marcel Dekker 2005, pp. 161-167.

The abrasive element can comprise one or more devices having helical elements, for example one screw or in particular two screws (so-called twin screw). The devices may be in a corotating or counterrotating arrangement. The devices may be in an interlocking or a non-interlocking arrangement. In addition to the helical elements, which generally serve primarily for conveyance, each device of the abrasive element can comprise further elements that usually serve primarily for mixing. Examples of such elements are kneading blocks. The device of the abrasive element usually has different zones of helical elements and mixing elements.

In one embodiment, a heat exchanger having a counterrotating twin screw is used as the extruder. In one embodiment, a heat exchanger having a corotating twin screw is used as the extruder. Preference is given to using as the extruder a heat exchanger having a corotating twin screw in which the screws are in an interlocking arrangement.

The menthol melt can be conveyed through the extruder by the rotation of the abrasive element or conveyed through the extruder with the additional assistance of e.g. a pump.

In one embodiment of the invention, the temperature of the extruder is set to below 42° C., preferably to a temperature from 5 to 40° C., in particular to a range from 10 to 32° C., in particular from 15 to 20° C. In a further embodiment, the temperature of the extruder can at the inlet and/or at the outlet be set to temperatures higher than in the region inbetween. The temperature can be set by means of a liquid coolant, in particular water. The menthol melt can be conveyed through the extruder in a single pass. It is likewise possible to circulate the menthol melt through the extruder multiple times until the desired proportion of seed crystals has been produced.

The present invention thus further provides the following embodiments:

1. A process for producing crystals of menthol, in particular L-menthol, wherein a menthol melt is conveyed through an extruder.
2. A process for producing a menthol melt, in particular an L-menthol melt, that comprises 0.1% to 50% by weight of seed crystals of menthol, wherein a menthol melt is conveyed through an extruder.
3. The process according to either of the preceding embodiments, wherein the abrasive element of the extruder comprises a device having helical elements.

4. The process according to any of the preceding embodiments, wherein the abrasive element of the extruder comprises more than one device, preferably two or three devices, having helical elements.
5. The process according to embodiment 4, wherein the abrasive element of the extruder is a twin screw.
6. The process according to any of the preceding embodiments, wherein the device comprises at least one helical element and at least one mixing element.
7. The process according to any of the preceding embodiments 4 to 6, wherein the devices are in a corotating arrangement.
8. The process according to any of the preceding embodiments 4 to 6, wherein the devices are in a counterrotating arrangement.
9. The process according to any of the preceding embodiments 4 to 8, wherein the devices are in an interlocking arrangement.
10. The process according to any of the preceding embodiments 4 to 8, wherein the devices are in a non-interlocking arrangement.
11. The process according to any of the preceding embodiments, wherein the menthol melt is conveyed through the heat exchanger through the rotation of the abrasive element.
12. The process according to any of the preceding embodiments, wherein the menthol melt is conveyed through the heat exchanger by means of a pump.
13. The process according to any of the preceding embodiments, wherein the temperature of the extruder is set to below 42° C., in particular to a range from 5 to 40° C., preferably 10 to 32° C.
14. A process for producing menthol particles, in which
    a. a menthol melt that contains seed crystals of menthol is produced by conveying a menthol melt through an extruder and
    b. the menthol melt thus obtained is brought into contact with at least one cooled surface.
15. The process according to embodiment 14, wherein a menthol melt obtained according to a process of embodiments 2 to 13 is used.
16. The process according to embodiment 14 or 15, wherein the menthol melt obtained is brought into contact with two spaced-apart cooled surfaces, preferably in the form of a double-belt cooler.

EXAMPLES

Grading system for evaluating caking:
0=completely free-flowing, no caking
1=slight caking that can be easily loosened by hand
2=severe caking that can be separated only with difficulty or not at all

1. INVENTIVE EXAMPLES

Examples 1A-3, 1B-1, and 1D-2

The menthol particles used were menthol flakes produced according to Examples A-3, B-1, and D2. Immediately after shaping, 20 kg of the menthol particles were transferred to bags made from polyethylene film 0.12 mm thick having the dimensions 660 mm [=L (bag)] by 690 mm [=W (bag)], the bags were sealed, and these bags were packed into boxes. The boxes used were made from double-walled corrugated cardboard having the internal dimensions: length 385 mm [=L (box)], width 320 mm [=W (box)], height 450 mm [=H (box)] and a corrugated cardboard thickness of 6 mm. The container compression resistance (DIN 55440) F of the box is 4500 N, the weight is 0.8 kg, the width of the prefabricated edge is 40 mm. It is a collapsible box according to FEFCO 0201. The boxes were closed with adhesive tape and stored on the area formed by L (box) and W (box) at 20° C. for 7 days. The boxes were then dropped onto the ground (concrete floor) from a height of 1.5 m. This was done by lifting the boxes to a height of 1.5 m with the aid of the transport arm of a dropping robot and then allowing them to fall freely onto the concrete floor. The area of impact of the box is the area of the box formed by L (box) and W (box).

The boxes thus treated were opened immediately after the input of mechanical energy and 18 weeks (storage at 20° C.) after the input of mechanical energy, and the degree of caking was assessed on the basis of the grading scale (see above): For all 3 examples 1A-3, 1B-1, and 1D-2, the degree of caking of the menthol particles was graded "0" both immediately after the input of mechanical energy and after 18 weeks.

Examples 2A-3, 2B-1, and 2D-2

Examples 1A-3, 1B-1, and 1D-2 were repeated, but with storage for 14 days before the input of mechanical energy.

The boxes thus treated were opened immediately after the input of mechanical energy and 17 and 18 weeks (storage at 20° C.) after the input of mechanical energy, and the degree of caking was assessed on the basis of the grading scale (see above): For all 3 examples 2A-3, 2B-1, and 2D-2, the degree of caking of the menthol particles was graded "0" both immediately after the input of mechanical energy and after 17 and 18 weeks.

Examples 3A-3, 3B-1, and 3D-2

Examples 1A-3, 1B-1, and 1D-2 were repeated, but with storage for 21 days before the input of mechanical energy.

The boxes thus treated were opened immediately after the input of mechanical energy and 16, 17, and 18 weeks (storage at 20° C.) after the input of mechanical energy, and the degree of caking was assessed on the basis of the grading scale (see above): For all 3 examples 3A-3, 3B-1, and 3D-2, the degree of caking of the menthol particles was graded "0" both immediately after the input of mechanical energy and after 16, 17, and 18 weeks.

Examples 4A-3, 4B-1, and 4D-2

Examples 2A-3, 2B-1, and 2D-2 were repeated, but with the boxes dropped from a height of 1.0 m.

The boxes thus treated were opened immediately after the input of mechanical energy and 18 weeks (storage at 20° C.) after the input of mechanical energy, and the degree of caking was assessed on the basis of the grading scale (see above): For all 3 examples 4A-3, 4B-1, and 4D-2, the degree of caking of the menthol particles was graded "0" both immediately after the input of mechanical energy and after 18 weeks.

Examples 5A-3, 5B-1, and 5D-2

Examples 2A-3, 2B-1, and 2D-2 were repeated, but with the boxes dropped from a height of 2.0 m.

The boxes thus treated were opened immediately after the input of mechanical energy and 18 weeks (storage at 20° C.) after the input of mechanical energy, and the degree of caking was assessed on the basis of the grading scale (see above): For all 3 examples 5A-3, 5B-1, and 5D-2, the degree of caking of the menthol particles was graded "0" both immediately after the input of mechanical energy and after 18 weeks.

Examples 6A-3, 6B-1, and 6D-2

Examples 2A-3, 2B-1, and 2D-2 were repeated, but in each case with 10 kg of the menthol particles transferred to bags immediately after shaping.

The boxes thus treated were opened immediately after the input of mechanical energy and 18 weeks (storage at 20° C.) after the input of mechanical energy, and the degree of caking was assessed on the basis of the grading scale (see above): For all 3 examples 6A-3, 6B-1, and 6D-2, the degree of caking of the menthol particles was graded "0" both immediately after the input of mechanical energy and after 18 weeks.

II. COMPARATIVE EXAMPLES

Examples C1A-3, C1B-1 and C1D-2-Menthol Particles without Input of Energy

The menthol particles used were menthol flakes produced according to Examples A-3, B-1, and D2. Immediately after shaping, 20 kg of the menthol particles were transferred to bags made from polyethylene film 0.12 mm thick having the dimensions 660 mm [=L (bag)] by 690 mm [=W (bag)], the bags were sealed, and these bags were packed into boxes. The boxes used were made from double-walled corrugated cardboard having the internal dimensions: length 385 mm [=L (box)], width 320 mm [=W (box)], height 450 mm [=H (box)] and a corrugated cardboard thickness of 6 mm. The container compression resistance (DIN 55440) F of the box is 4500 N, the weight is 0.8 kg, the width of the prefabricated edge is 40 mm. It is a collapsible box according to FEFCO 0201. The boxes were closed with adhesive tape and stored on the area formed by L (box) and W (box) at 20° C.

The boxes were opened 18 and 19 weeks after filling and the degree of caking was assessed on the basis of the grading scale (see above): For all 3 comparative examples C1A-3, C1B-1, and C1D-2, the degree of caking of the menthol particles was graded "2" after both 18 and 19 weeks.

Examples C2A-3, C2B-1, and C2D-2-Menthol Particles with Input of Energy Input Immediately after Shaping The menthol particles used were menthol flakes produced according to Examples A-3, B-1, and D2. Immediately after shaping, 20 kg of the menthol particles were transferred to bags made from polyethylene film 0.12 mm thick having the dimensions 660 mm [=L (bag)] by 690 mm [=W (bag)], the bags were sealed, and these bags were packed into boxes. The boxes used were made from double-walled corrugated cardboard having the internal dimensions: length 385 mm [=L (box)], width 320 mm [=W (box)], height 450 mm [=H (box)] and a corrugated cardboard thickness of 6 mm. The container compression resistance (DIN 55440) F of the box is 4500 N, the weight is 0.8 kg, the width of the prefabricated edge is 40 mm. It is a collapsible box according to FEFCO 0201. The boxes were closed with adhesive tape and stored on the area formed by L (box) and W (box) at 20° C. for 2 hours. The boxes were then dropped onto the ground (concrete floor) from a height of 1.5 m. This was done by lifting the boxes to a height of 1.5 m with the aid of the transport arm of a dropping robot and then allowing them to fall freely onto the concrete floor. The area of impact of the box is the area of the box formed by L (box) and W (box).

The boxes thus treated were opened immediately after the input of mechanical energy and 18 and 19 weeks (storage at 20° C.) after the input of mechanical energy, and the degree of caking was assessed on the basis of the grading scale (see above): For all 3 comparative examples C2A-3, C2B1, and C2D-2, the degree of caking of the menthol particles was graded "0" immediately after the input of mechanical energy and "2" after both 18 and 19 weeks.

In other words, the input of mechanical energy in accordance with the invention results in a decrease in caking, but this persists only if storage in accordance with the invention had taken place prior to the input of mechanical energy.

III. Examples for Menthol Particles that can be Used in the Process of the Invention Example A-1

An L-menthol melt heated to 50° C. was introduced into a scraped-surface cooler thermostatically controlled at 10° C. The scraped-surface cooler was used to produce menthol seed crystals; the seed crystal content was determined by measuring the density and adjusted to 20% by weight. The thus obtained suspension of molten menthol and 20% by weight of menthol seed crystals was discharged and applied via a thermostatically controlled pipeline to a double-sided cooling belt thermostatically controlled at 15° C. on both sides, the belt gap being set at 4 mm. After a running time of 240 s, a crystallized film of L-menthol 4 mm thick was obtained at the end of the belt, which was comminuted by a crusher into flakes having an edge length from 5 to 25 mm. Flakes that were shiny in appearance and had an average thickness of 4 mm were obtained on both sides. The flakes thus obtained had an edge length within a range from 5 to 25 mm, the majority of the flakes having an edge length within a range from 10 to 16 mm.

Example A-2

An L-menthol melt heated to 50° C. was introduced into a scraped-surface cooler thermostatically controlled at 10° C. The scraped-surface cooler was used to produce menthol seed crystals; the seed crystal content was determined by measuring the density and adjusted to 20% by weight. The thus obtained suspension of molten menthol and 20% by weight of menthol seed crystals was discharged and applied via a thermostatically controlled pipeline to a double-sided cooling belt thermostatically controlled at 15° C. on both sides, the belt gap being set at 6 mm. After a running time of 240 s, a crystallized film of L-menthol 6 mm thick was obtained at the end of the belt, which was comminuted by a crusher into flakes having an edge length from 5 to 25 mm. Flakes that were shiny in appearance and had an average thickness of 6 mm were obtained on both sides. The flakes thus obtained had an edge length within a range from 5 to 25 mm, the majority of the flakes having an edge length within a range from 10 to 16 mm.

Example A-3

An L-menthol melt heated to 50° C. was introduced into a scraped-surface cooler thermostatically controlled at 10° C. The scraped-surface cooler was used to produce menthol seed crystals; the seed crystal content was determined by measuring the density and adjusted to 20% by weight. The thus obtained suspension of molten menthol and 20% by weight of menthol seed crystals was discharged and applied via a thermostatically controlled pipeline to a double-sided cooling belt thermostatically controlled at 15° C. on both sides, the belt gap being set at 8 mm. After a running time of 240 s, a crystallized film of L-menthol 8 mm thick was obtained at the end of the belt, which was comminuted by a crusher into flakes having an edge length from 5 to 25 mm. Flakes that were shiny in appearance and had an average thickness of 8 mm were obtained on both sides. The flakes thus obtained had an edge length within a range from 5 to 25 mm, the majority of the flakes having an edge length within a range from 10 to 16 mm.

Example B-1

An L-menthol melt heated to 50° C. was introduced into a scraped-surface cooler thermostatically controlled at 20° C. The scraped-surface cooler was used to produce menthol seed crystals. The seed crystal content was determined by measuring the density and adjusted to 10% by weight. The thus obtained suspension of molten menthol and 10% by weight of menthol seed crystals was discharged and applied via a thermostatically controlled pipeline to a double-sided cooling belt thermostatically controlled at 15° C. on both sides, the belt gap being set at 6 mm. After a running time of 240 to 300 s, a crystallized film of L-menthol 6 mm thick was obtained at the end of the belt. Precomminution with a pin crusher with subsequent comminution using a sieve grinder (model 250 D rotor fine granulator, manufacturer Alexanderwerk, using a sieve insert of 12×24 mm) afforded menthol flakes of the desired size. After subsequent separation of fines using a 4 mm sieve, menthol flakes having the following size distribution were obtained:

|  | Thickness in mm | Length in mm | Width in mm |
|---|---|---|---|
| Mean | 5.3 | 15.3 | 11.5 |
| MAX | 10.5 | 22.4 | 19.0 |
| MIN | 2.3 | 7.6 | 5.7 |

The proportion of menthol particles under 4 mm in size was <0.1% by weight.

Example B-2

An L-menthol melt heated to 50° C. was introduced into a scraped-surface cooler thermostatically controlled at 20° C. The scraped-surface cooler was used to produce menthol seed crystals. The seed crystal content was determined by measuring the density and adjusted to 10% by weight. The thus obtained suspension of molten menthol and 10% by weight of menthol seed crystals was discharged and applied via a thermostatically controlled pipeline to a double-sided cooling belt thermostatically controlled at 15° C. on both sides, the belt gap being set at 8 mm. After a running time of 240 to 300 s, a crystallized film of L-menthol 8 mm thick was obtained at the end of the belt. Precomminution with a pin crusher with subsequent comminution using a sieve grinder (model 250 D rotor fine granulator, manufacturer Alexanderwerk, using a sieve insert of 12×24 mm) afforded menthol flakes of the following size distribution.

|  | Thickness in mm | Length in mm | Width in mm |
|---|---|---|---|
| Mean | 7.2 | 15.2 | 10.5 |
| MAX | 14.2 | 21.4 | 18.5 |
| MIN | 0.3 | 0.54 | 0.2 |

The proportion of menthol particles under 4 mm in size was 12% by weight.

Example B-3

An L-menthol melt heated to 50° C. was introduced into a scraped-surface cooler thermostatically controlled at 20° C. The scraped-surface cooler was used to produce menthol seed crystals. The seed crystal content was determined by measuring the density and adjusted to 10% by weight. The thus obtained suspension of molten menthol and 10% by weight of menthol seed crystals was discharged and applied via a thermostatically controlled pipeline to a double-sided cooling belt thermostatically controlled at 15° C. on both sides, the belt gap being set at 9 mm. After a running time of 240 to 300 s, a crystallized film of L-menthol 9 mm thick was obtained at the end of the belt. Precomminution with a pin crusher with subsequent comminution using a sieve grinder (model 250 D rotor fine granulator, manufacturer Alexanderwerk, using a sieve insert of 12×24 mm) afforded menthol flakes of the desired size. After subsequent separation of fines using a 4 mm sieve, menthol flakes having the following size distribution were obtained:

|  | Thickness in mm | Length in mm | Width in mm |
|---|---|---|---|
| Mean | 8.9 | 15.5 | 12.0 |
| MAX | 17.2 | 21.0 | 19.3 |
| MIN | 4.2 | 7.4 | 5.7 |

The proportion of menthol particles under 4 mm in size was <0.1% by weight.

Example C-1

An L-menthol melt heated to 50° C. was fed into an extruder cooled to 15° C. (with corotating twin screw and integrated pump for conveying the L-menthol melt, outflow temperature of 42° C.) and the extruder used to produce menthol seed crystals. The seed crystal content was determined by measuring the density and adjusted to 30% by weight The thus obtained suspension of molten menthol and 30% by weight of menthol seed crystals was discharged and applied via a thermostatically controlled pipeline to a double-sided cooling belt thermostatically controlled at 15° C. on both sides, the belt gap being set at 6 mm. After a running time of 160 s, a crystallized film of L-menthol 6 mm thick was obtained at the end of the belt. Precomminution with a pin crusher with subsequent comminution using a sieve grinder (model 250 D rotor fine granulator, manufacturer Alexanderwerk, using a sieve insert of 12×24 mm) afforded menthol flakes of the desired size. After subsequent separation of fines using a 4 mm sieve, menthol flakes having the following size distribution were obtained:

|      | Thickness in mm | Length in mm | Width in mm |
|------|-----------------|--------------|-------------|
| Mean | 5.6             | 15.4         | 11.2        |
| MAX  | 10.7            | 22.7         | 19.0        |
| MIN  | 2.1             | 7.3          | 5.8         |

The proportion of menthol particles under 4 mm in size was <0.1% by weight.

Example C-2

An L-menthol melt heated to 50° C. was fed into an extruder cooled to 15° C. (with corotating twin screw and integrated pump for conveying the L-menthol melt, outflow temperature of 42° C.) and the extruder used to produce menthol seed crystals. The seed crystal content was determined by measuring the density and adjusted to 30% by weight. The thus obtained suspension of molten menthol and 30% by weight of menthol seed crystals was discharged and applied via a thermostatically controlled pipeline to a double-sided cooling belt thermostatically controlled at 15° C. on both sides, with the belt gap set at 8 mm. After a running time of 240 s, a crystallized film of L-menthol 8 mm thick was obtained at the end of the belt. Precomminution with a pin crusher with subsequent comminution using a sieve grinder (model 250 D rotor fine granulator, manufacturer Alexanderwerk, using a sieve insert of 12×24 mm) afforded menthol flakes of the desired size. After subsequent separation of fines using a 4 mm sieve, menthol flakes having the following size distribution were obtained:

|      | Thickness in mm | Length in mm | Width in mm |
|------|-----------------|--------------|-------------|
| Mean | 7.6             | 15.2         | 10.3        |
| MAX  | 14.3            | 20.4         | 19.5        |
| MIN  | 3.7             | 7.5          | 5.2         |

The proportion of menthol particles under 4 mm in size was <0.1% by weight.

Example D-1

An L-menthol melt heated to 50° C. was fed into an extruder cooled to 20° C. (with corotating twin screw and integrated pump for conveying the L-menthol melt, outflow temperature of 42° C.) and the extruder used to produce menthol seed crystals. The seed crystal content was determined by measuring the density and adjusted to 20% by weight. The suspension of molten menthol and 20% by weight of menthol seed crystals thus obtained was discharged and applied via a thermostatically controlled pipeline to a double-sided cooling belt thermostatically controlled at 15° C. on both sides, the belt gap being set at 7 mm. After a running time of 240 s, a crystallized film of L-menthol 7 mm thick was obtained at the end of the belt. Precomminution with a pin crusher with subsequent comminution using a sieve grinder (model 250 D rotor fine granulator, manufacturer Alexanderwerk, using a sieve insert of 12×24 mm) afforded menthol flakes of the desired size. After subsequent separation of fines using a 4 mm sieve, menthol flakes having the following size distribution were obtained:

|      | Thickness in mm | Length in mm | Width in mm |
|------|-----------------|--------------|-------------|
| Mean | 6.8             | 15.5         | 11.3        |
| MAX  | 17.5            | 23.0         | 19.7        |
| MIN  | 4.1             | 6.8          | 5.2         |

The proportion of menthol particles under 4 mm in size was <0.1% by weight.

Example D-2

An L-menthol melt heated to 50° C. was fed into an extruder cooled to 20° C. (with corotating twin screw and integrated pump for conveying the L-menthol melt, outflow temperature of 42° C.) and the extruder used to produce menthol seed crystals. The seed crystal content was determined by measuring the density and adjusted to 20% by weight. The suspension of molten menthol and 20% by weight of menthol seed crystals thus obtained was discharged and applied via a thermostatically controlled pipeline to a double-sided cooling belt thermostatically controlled at 15° C. on both sides, the belt gap being set at 9 mm. After a running time of 240 s, a crystallized film of L-menthol 9 mm thick was obtained at the end of the belt. Precomminution with a pin crusher with subsequent comminution using a sieve grinder (model 250 D rotor fine granulator, manufacturer Alexanderwerk, using a sieve insert of 12×24 mm) afforded menthol flakes having the following size distribution.

|      | Thickness in mm | Length in mm | Width in mm |
|------|-----------------|--------------|-------------|
| Mean | 8.8             | 15.2         | 11.0        |
| MAX  | 17.5            | 21.3         | 19.7        |
| MIN  | 0.3             | 0.5          | 0.2         |

The proportion of menthol particles under 4 mm in size was 13% by weight.

The invention claimed is:

1. A process for producing menthol particles stabilized against caking, said process comprising storing menthol particles, following shaping, for at least 7 days at a temperature of 0 to 30° C., after which the menthol particles are supplied with at least as much mechanical energy as they receive when
   20 kg of said menthol particles
   are packed into a bag made from polyethylene film 0.12 mm thick having the dimensions length L (bag) 660 mm and width W (bag) 690 mm, sealing the bag;
   said bag is packed into a cuboidal box made from double-walled corrugated cardboard having the internal dimensions length L (box) 385 mm, width W (box) 320 mm, and height H (box) 450 mm and a corrugated cardboard thickness of 6 mm, and
   said box is dropped once from a height of 1.0 m onto an inelastic surface plane-parallel to the side formed by L (box) and H (box).

2. The process according to claim 1, wherein the number of particles at the end of the process is still at least 50% of the number of particles employed at the start of the process.

3. The process according to claim 1, wherein at least 50% by weight of the menthol particles stabilized against caking are of the same shape as the menthol particles employed.

4. The process according to claim 1, wherein at least 50% by weight of the menthol particles stabilized against caking are of the same size as the menthol particles employed.

5. The process according to claim 1, wherein menthol in the menthol particles is present in the form of L-menthol.

6. The process according to claim 1, wherein the menthol content of the menthol particles is more than 80% by weight based on the total weight of the particle.

7. The process according to claim 1, wherein menthol particles are used that have a size within a range from 1 to 35 mm.

8. The process according to claim 1, wherein menthol particles in the form of flakes, spheres or pellets are used.

9. The process according to claim 1, wherein menthol particles in the form of flakes are used that have a thickness from 0.2 to 15 mm.

10. The process according to claim 1, wherein menthol in the form of flakes is used as menthol particles that are obtained by contacting a menthol melt with two spaced-apart cooled surfaces, this being accompanied by solidification of the menthol melt into menthol, with the contact between the solidifying menthol melt and the cooled surfaces maintained at least until solidification is complete.

11. The process according to claim 10, wherein 0.1% to 50% by weight of seed crystals of menthol are mixed into the menthol melt to be used before it is contacted with the cooled surfaces.

12. The process according to claim 11, wherein the seed crystals are formed by treatment in a scraped-surface cooler or an extruder of the menthol melt to be used.

13. The process according claim 10, wherein the two cooled surfaces have a plane-parallel orientation and are spaced apart at a distance of 0.2 to 15 mm.

\* \* \* \* \*